US00PP36001P2

(12) United States Plant Patent
Hansen

(10) Patent No.: US PP36,001 P2
(45) Date of Patent: Jul. 9, 2024

(54) ***AGASTACHE* PLANT NAMED 'Guava Lava'**

(50) Latin Name: ***Agastache* hybrid**
Varietal Denomination: Guava Lava

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 18/445,667

(22) Filed: Dec. 15, 2023

(51) Int. Cl.
*A01H 5/02* (2018.01)
*A01H 6/50* (2018.01)

(52) U.S. Cl.
USPC ..... Plt./399

(58) Field of Classification Search
USPC ..... Plt./263.1, 399
See application file for complete search history.

*Primary Examiner* — Karen M Redden

(57) ABSTRACT

A new and unique cultivar of hyssop, *Agastache* plant named 'Guava Lava' with medium-sized, dense, rounded, well-branched habit. The flowers cover the top two-thirds of the plant, are large, coral-orangish-colored, with mauve-pink calyxes in densely branched panicles over an extended period beginning in early summer. The new plant is useful in the landscape and as a cut flower.

1 Drawing Sheet

Botanical denomination: *Agastache* hybrid.
Variety designation: 'Guava Lava'.

STATEMENT REGARDING PRIOR DISCLOSURES UNDER 37 CFR 1.77(B)(6)

The first non-enabling disclosure of the claimed plant was made by Walters Gardens, Inc. on Feb. 1, 2023, in the form of a website brief description and photograph followed by a short description. Walters Gardens, Inc. obtained the new plant and information about the new plant directly from the inventor. The first offer for sale of the new plant was on Feb. 6, 2023. No plants of *Agastache* 'Guava Lava' have been sold or offered for sale in this country or anywhere in the world nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct Anise Hyssop plant or Hummingbird Mint from the genus *Agastache* and given the cultivar name 'Guava Lava'. The new plant was the result of a single seedling selection from a cross on Jun. 8, 2017, by the inventor between the proprietary, unreleased, hybrid, 16-3-1 (not patented) as the female or seed parent and the proprietary, unreleased, proprietary hybrid 16-4-1 (not patented) as the male or pollen parent. The seeds from the pollination were collected in the late summer of 2017. The individually selected seedling was eventually given the breeder code 17-9-1 after being first isolated from trials at a nursery in Zeeland, MI during the summer of 2019. It was selected for the final introduction in the summer of 2020.

*Agastache* 'Guava Lava' has been asexually propagated at the same nursery in Zeeland, MI originally by basal shoot cuttings in 2018, followed by traditional shoot tip and stem cutting procedures and found to reproduce plants that are identical and exhibit all the characteristics of the original plant in successive generations of asexual propagation.

The new plant, *Agastache* 'Guava Lava', has not been observed under all possible environments. The phenotype may vary slightly with different environmental conditions, such as temperature, light, fertility, moisture and maturity levels, but without any change in the genotype.

In comparison to the new plant, the seed parent has a taller habit, darker reddish flowers, and the flowers were smaller. The male parent has a lighter colored flower.

The nearest comparison varieties known to the inventor are: 'Peachie Keen' U.S. Plant Pat. No. 25,886, 'Mango Tango' U.S. Plant Pat. No. 28,747, 'Kudos Coral' U.S. Plant Pat. No. 25,613, 'Kudos Mandarin' U.S. Plant Pat. No. 25,381, 'Apricot Sprite' (not patented), and 'Summer Sunset' U.S. Plant Pat. No. 23,623.

'Peachie Keen' has a similar habit in both height and width but with apricot-peach-colored flowers and purplish-pink calyxes. 'Mango Tango' has a shorter and more compact habit and the flowers are light peach to mango-orange colored. 'Kudos Mandarin' has deeper orange-colored flowers with a significantly smaller habit. 'Kudos Coral' has a narrower and smaller habit in both height and width, and the flower color is more reddish-colored. 'Apricot Sprite' has a slightly smaller habit with flowers of bright orange. 'Summer Sunset' is less winter-hardy, has a smaller and narrower habit, and the flower color are more orangish colored. Both 'Kudos Mandarin' and 'Kudos Coral' have not overwintered under similar conditions where the new plant has survived the winter.

*Agastache* 'Guava Lava' is distinct from the parents and all other anise hyssop known to the inventor in the following combined traits:

1. Medium-sized, dense, well-branched, rounded, full, habit;
2. Large flowers of coral-orangish coloration in densely branched panicles;
3. Long bloom time with effectiveness extended by persistent, mauve-pink-colored calyxes;

4. Foliage is medium green;
5. Flowers covering the upper two-thirds of the plant beginning in early summer and continuing to fall.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source, and direction may cause the appearance of minor variations in color.

DETAILED PLANT DESCRIPTION

Figure 1:
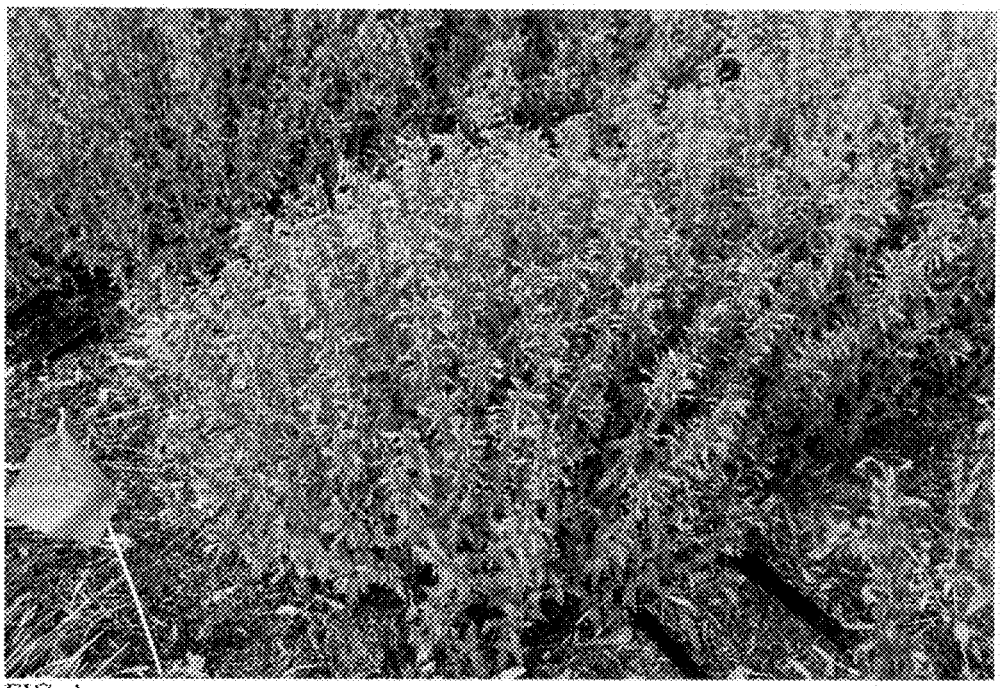
FIG. 1 shows a landscape view of a two-year-old plant in mid-season flower in an overwintered trial block at a nursery near Zeeland, Michigan.
Figure 2:
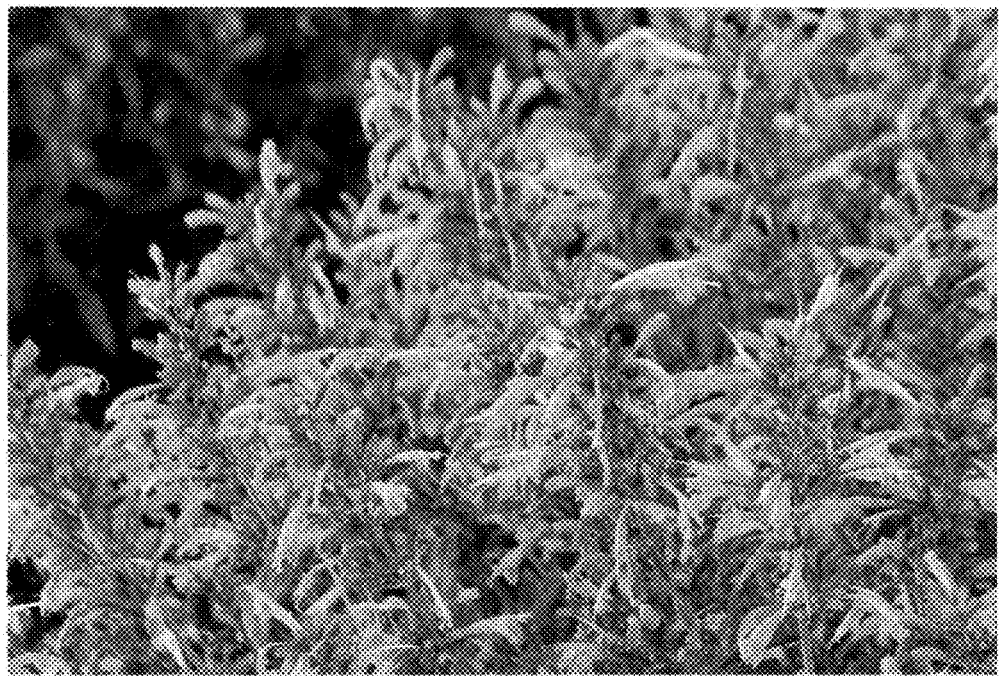
FIG. 2 shows a close-up of the scapes with flowers, buds, and calyxes.

The following is a detailed description of the new *Agastache* cultivar 'Guava Lava' based on observations of a three-year-old specimen grown with supplemental watering and fertilizer as needed in a display garden at a wholesale perennial nursery in Zeeland, MI. Color descriptions are from the 2015 edition of The Royal Horticultural Society Colour Chart except where common dictionary terms are used.

Parentage: The female or seed parent is the unreleased, non-patented, proprietary hibiscus known by the breeder code 16-3-1 (not patented), the male or pollen parent is the unreleased, non-patented, proprietary hibiscus known by the breeder code 16-4-1 (not patented);

Propagation:

*Method*.—Basal shoot cuttings.

*Time to initiate roots*.—About 10 days.

*Crop time*.—Finishing in a 3.8-liter pot from a 25 mm plug in 10 to 12 weeks.

Plant habit: Multi-stemmed herbaceous perennial, rounded, heavily branched;

Plant size: Without growth retardants or pinching — to about 65 cm tall and 82 cm across;

Roots: Fibrous, well-branched; to about 2 mm diameter near the base; color light tan nearest RHS 165D depending on soil type;

Stem: Quadrangular; fistulous; stiff; wiry; micro-puberulent; to about 6 mm across at the base and 65 cm tall with flowering starting about 25 cm above the soil; seven internodes below center main peduncle; internodes average about 3.5 cm long; about eight to ten stems per plant;

Primary branches: Quadrangular; opposite; about ten to twelve per stem; to about 40 cm long and about 3 mm diameter at base;

Secondary branches: Quadrangular; opposite; up to six per primary branch; to about 32 cm long and 2.5 mm diameter at base;

Primary and secondary branch color: Proximal portions nearest RHS 138A, distal portions nearest RHS NN137B; nodes nearest RHS 200A;

Leaf: Simple; opposite; broadly lanceolate; base rounded; apex narrowly acute; margin irregularly serrate to entire; adaxial glabrous and matte, abaxial micro-glandular and matte;

Leaf size: To about 44 mm long and 18 mm across near base, decreasing distally;

Leaf color: Young expanding adaxial nearest RHS 138A, abaxial between RHS 147C and 138B; mature adaxial between RHS 137A and RHS NN137C, abaxial nearest RHS 147C;

Leaf venation: Reticulate; glabrous and slightly impressed adaxial, puberulent and costate abaxial;

Vein color: Adaxial nearest RHS 137A, abaxial midrib nearest RHS 145D and secondary veins nearest RHS 147B;

Leaf fragrance: Moderately herbal, minty;

Petiole: Glabrous adaxial and micro-puberulent to micro-glandular abaxial; concavo-convex; to 6 mm long and 2 mm across, average 4 mm long and 1.5 mm;

Petiole color: Adaxial nearest RHS 137B; abaxial nearest RHS 138A;

Inflorescence: In densely branched panicle with short branches or whorls in axils; 8 to 60 flowers on two short branchlets per node; up to 12 nodes per central stem, and 2,000 to 3,000 flowers per main stem; terminal flowering portion about 28 cm long and about 7.5 cm across; total inflorescence flowering portion about 42 cm long and about 40 cm across; each stem flowering for about 5 weeks but remain effective for about 6 weeks or more because of the strongly pigmented persistent calyxes; repeating if deadheaded;

Bloom period: Early summer through frost in Zeeland, Michigan;

Peduncle: Average about 65 cm tall and about 7 mm at base; puberulent; heavily branched; attitude upward;

Peduncle color: Nearest RHS 146C proximally and nearest RHS NN137B distally;

Pedicel: Cylindrical; short; micro-glandular to micro-puberulent; matte; to about 2 mm long and 0.5 mm diameter; attitude mostly upright; color nearest RHS N77C;

Flower: Perfect; complete; zygomorphic; sympetalous; bilabiate, with five united petals forming an upper labium 2-lobed and lower labium 3-lobed; attitude outwardly to slightly upwardly;

Flower size: About 29 mm long to exerted stamens and style, about 8 mm tall and 5 mm across; corolla to about 24 mm long, 7 mm tall, 5 mm across, 3 mm diameter at fusion of two labium, and 1 mm diameter at base;

Flower lasting: Individual flowers open for about 3 days; individual panicle lasting for about 5 weeks;

Bud on day prior to opening: Arcuate, clavate to obelliptical; about 21 mm long, 4 mm tall, and 3 mm wide just before the apex and 1.5 mm wide at base;

Bud color: Petals nearest RHS 180B toward apex, proximal portion nearest RHS 179B; calyx distal free portion nearest RHS 64A, central dorsal portion nearest RHS 71A with veins nearest RHS N79B, and ventral portion nearest RHS 161D;

Petals: Both upper and lower labium glabrous adaxial, micro-puberulent to micro-glandular abaxial; matte both adaxial and abaxial; both labia proximally fused forming tube in the basal 19 mm;

Upper labium: 2-lobed, about 22 mm long and 4 mm across toward apex; lobes centrally cleft about 1.5 mm deep and 2 mm across at base; lobe apices rounded; margin entire;

Lower labium: 3-lobed; about 24 mm long, 3 mm wide at fusion and 5 mm across near apex; arcuate downward in distal 5 mm; center lobe concavo-convex, about 4 mm long and 4 mm across, with a rounded emarginate apex 1 mm deep, and crenate margin; two side lobes of lower petal spread horizontally, about 3 mm long and 2 mm wide, with rounded apex and entire margin;

Petal color: Abaxial and adaxial upper labium nearest RHS 180D, lower labium adaxial nearest RHS 185C, lower labium abaxial nearest RHS 185D; corolla tube adaxial dorsal portion nearest RHS N170D and the ventral portion between RHS 24D and RHS 168D, the abaxial ventral portion nearest RHS N170C and the dorsal portion between RHS 180D and RHS 181C; color not changing with maturity;

Calyx: Tubular; about 6 mm long and diameter about 2 mm;

Sepals: Five; linear; acute apices; entire margin; fused into tube in basal 5 mm; glabrous adaxial and micro-glandular to micro-puberulent abaxial; to about 6 mm long, and 1 mm across at fusion;

Calyx color: Adaxial between RHS N81C and RHS N81D in distal 0.5 to 1 mm and proximally nearest RHS 148D; abaxial nearest RHS N77C distally and nearest RHS 195D proximally;

Gynoecium: Single; to 31 mm long; exerted;

*Style*.—One, about 29 mm long and about 0.3 mm diameter; terete; glabrous; straight; color distal 2 to 3 mm lighter than RHS N81D, proximally nearest RHS NN155D becoming blushed with nearest RHS N81D as flower matures.

*Stigma*.—Bifid and reflex; each segment about 1 mm long and about 0.3 mm diameter; tapering to a pointed apex; color between RHS N81B and RHS nearest RHS 5D.

Androecium:

*Stamen*.—In two sets of two, exerted, adnate to the inner corolla.

*Filaments*.—Two longer and two shorter; paired and exerted; longer pair adnate in the basal 12 mm and free in the proximal 11 mm; shorter pair adnate in the basal 13 mm and free in the proximal 8 mm; color between RHS N80C and RHS N81D.

*Anthers*.—Dorsifixed; versatile; folded; longitudinal; about 1.2 mm long and about 1 mm across; color nearest RHS 186C.

Pollen: Abundant; color nearest RHS NN155B;

Fragrance: None detected;

Fruit: Two carpels;

Seed: Nutlet, typically one to two per naturally pollinated flower, ellipsoidal; about 1 mm long, 0.8 mm across and 0.5 mm thick;

Seed color: Nearest 202A;

Resistance: 'Guava Lava' is resistant to *Odocoileus hemionus* browsing but has not been tested or shown resistance to other pests and diseases common to *Agastache*.

Hardiness: The new plant has survived USDA hardiness zones 6 to 10 but has not been tested yet beyond these temperatures.

It is claimed:

1. A new and distinct cultivar of *Agastache* plant named 'Guava Lava' as herein described and photographed.

* * * * *